(12) United States Patent
Kamo et al.

(10) Patent No.: US 10,307,996 B2
(45) Date of Patent: Jun. 4, 2019

(54) NANO THIN-FILM TRANSFER SHEET, METHOD FOR MANUFACTURING NANO THIN-FILM TRANSFER SHEET, AND METHOD FOR TRANSFERRING NANO THIN-FILM LAYER INTO ADHEREND

(71) Applicant: HITACHI CHEMICAL COMPANY, LTD., Tokyo (JP)

(72) Inventors: Kazuyuki Kamo, Tsukuba (JP); Nobuaki Takane, Tsukuba (JP)

(73) Assignee: HITACHI CHEMICAL COMPANY, LTD, Tokyo (JP)

( * ) Notice: Subject to any disclaimer, the term of this patent is extended or adjusted under 35 U.S.C. 154(b) by 763 days.

(21) Appl. No.: 14/766,305

(22) PCT Filed: Jun. 6, 2013

(86) PCT No.: PCT/JP2013/065680
§ 371 (c)(1),
(2) Date: Aug. 6, 2015

(87) PCT Pub. No.: WO2014/122806
PCT Pub. Date: Aug. 14, 2014

(65) Prior Publication Data
US 2016/0031192 A1   Feb. 4, 2016

(30) Foreign Application Priority Data

Feb. 8, 2013  (JP) .................. 2013-023180

(51) Int. Cl.
*B32B 27/08*   (2006.01)
*B32B 37/00*   (2006.01)
(Continued)

(52) U.S. Cl.
CPC .............. *B32B 27/08* (2013.01); *A45D 44/22* (2013.01); *A61K 8/02* (2013.01); *A61K 8/0233* (2013.01);
(Continued)

(58) Field of Classification Search
CPC .............. A45D 44/22; A61K 2800/413; A61K 2800/5424; A61K 2800/5426; A61K 8/02;
(Continued)

(56) References Cited

U.S. PATENT DOCUMENTS 6,419,935 B1 *  7/2002  Gueret ................. A61K 8/0208
                                                    424/401
2008/0241926 A1 * 10/2008  Lee ...................... C12N 5/0068
                                                    435/395

(Continued)

FOREIGN PATENT DOCUMENTS

JP   2-107247 A   4/1990
JP   11-78389 A   3/1999
(Continued)

OTHER PUBLICATIONS

Office Action JP Patent Application No. P2013-023180 dated Mar. 21, 2017.
(Continued)

*Primary Examiner* — Jennifer A Steele
(74) *Attorney, Agent, or Firm* — Fitch, Even, Tabin & Flannery, L.L.P.

(57) ABSTRACT

The present invention relates to a nano thin-film transfer sheet comprising a permeable base, a soluble support layer, and a nano thin-film layer in this order, wherein the permeable base is a base which allows a solvent dissolving the soluble support layer to permeate or penetrate therethrough.

10 Claims, 3 Drawing Sheets

(51) Int. Cl.

| | | |
|---|---|---|
| *B32B 38/00* | (2006.01) | |
| *A61Q 19/08* | (2006.01) | |
| *A61K 8/02* | (2006.01) | |
| *B32B 5/02* | (2006.01) | |
| *A61K 8/73* | (2006.01) | |
| *A61K 8/81* | (2006.01) | |
| *A45D 44/22* | (2006.01) | |
| *A61Q 19/00* | (2006.01) | |
| *B32B 7/06* | (2019.01) | |
| *A61K 8/85* | (2006.01) | |
| *B32B 38/16* | (2006.01) | |
| *B32B 38/10* | (2006.01) | |

(52) U.S. Cl.
CPC ............ *A61K 8/736* (2013.01); *A61K 8/8129* (2013.01); *A61K 8/85* (2013.01); *A61Q 19/00* (2013.01); *A61Q 19/08* (2013.01); *B32B 5/028* (2013.01); *B32B 7/06* (2013.01); *B32B 37/0038* (2013.01); *B32B 37/025* (2013.01); *B32B 38/10* (2013.01); *A61K 2800/413* (2013.01); *A61K 2800/5424* (2013.01); *A61K 2800/5426* (2013.01); *B32B 2038/168* (2013.01); *B32B 2307/726* (2013.01); *B32B 2307/732* (2013.01); *B32B 2307/748* (2013.01); *B32B 2555/00* (2013.01)

(58) Field of Classification Search
CPC .... A61K 8/0233; A61K 8/736; A61K 8/8129; A61K 8/85; A61Q 19/00; A61Q 19/08; B32B 2038/168; B32B 2307/726; B32B 2307/732; B32B 2307/748; B32B 2555/00; B32B 27/08; B32B 37/0038; B32B 37/025; B32B 38/10; B32B 5/028; B32B 7/06; Y10T 428/1476; Y10T 428/2486
See application file for complete search history.

(56) References Cited

U.S. PATENT DOCUMENTS

| | | | | |
|---|---|---|---|---|
| 2010/0143677 | A1* | 6/2010 | Lee | ............ A61K 8/0208 |
| | | | | 428/212 |
| 2010/0150976 | A1* | 6/2010 | Schnitzler | ............ A61K 8/0208 |
| | | | | 424/401 |
| 2012/0080147 | A1* | 4/2012 | Offeman | ............ B01D 71/80 |
| | | | | 156/305 |
| 2014/0004170 | A1* | 1/2014 | Krohen | ............ A61L 27/34 |
| | | | | 424/423 |

FOREIGN PATENT DOCUMENTS

| | | |
|---|---|---|
| JP | 3215852 B2 | 10/2001 |
| JP | 2007-10929 A | 1/2007 |
| JP | 2008-049609 A | 3/2008 |
| JP | 4302321 B2 | 7/2009 |
| JP | 2012-236125 A | 12/2012 |
| WO | 2008/050913 A1 | 5/2008 |
| WO | WO 2011151417 A1 * 12/2011 ............ A61L 27/34 |

OTHER PUBLICATIONS

A.C. Fou et al., "Fabrication and properties of light-emitting diodes based on self-assembled mutlilayers of poly (phenylene vinylene)", Journal of Applied Physics, May 15, 1996, p. 7501-7509, vol. 79.

Al Lin Chun, "Nanosheets: Fit to Repair, Nature Nanotechnology," Jun. 16, 2009, p. 1-2.

T. Fujie, et al., "Adhesive, Flexible, and Robust Polysaccharide Nanosheets Integrated for Tisse-Defect Repair," Advanced Functional Materials, Aug. 24, 2009, p. 2560-2568, vol. 19.

International Preliminary Report on Patentability, dated Aug. 20, 2015, PCT/JP2013/065680 with English Translation submitted herewith (7pgs).

International Search Report, dated Sep. 10, 2013 for PCT/JP2013/065680 (2pgs).

* cited by examiner

NANO THIN-FILM TRANSFER SHEET, METHOD FOR MANUFACTURING NANO THIN-FILM TRANSFER SHEET, AND METHOD FOR TRANSFERRING NANO THIN-FILM LAYER INTO ADHEREND

TECHNICAL FIELD

The present invention relates to a nano thin-film transfer sheet, a method for manufacturing a nano thin-film transfer sheet, and a method for transferring a nano-thin film layer of a nano thin-film transfer sheet onto an adherend.

BACKGROUND ART

In recent years, cosmetic sheets intended to for improvement of skin luster, moistness and whiteness, prevention of wrinkles, or the like have attracted attention in accordance with enhancement in the quality of life. As such a cosmetic sheet, a wrinkles-improving sheet formed by allowing a moisturizing agent or the like to adhere onto wood fiber-derived paper has been suggested (see, for example, Patent Literature 1). The wrinkles-improving sheet is easy to break because its base is paper, and tends to be inferior in fitting feeling such as uncomfortable feeling in fitting because its adhesion onto the skin is not sufficient.

In contrast, as cosmetic materials for sheet packs or the like, use of natural raw materials derived from casein and silk has been considered. Also, in Non Patent Literature 1, a skin adhesive nano thin-film transfer sheet prepared by laminating chitosan and alginic acid alternately is described. The skin adhesive thin-film transfer sheet described in Non Patent Literature 1 can adhere onto the skin without any necessity of a pressure-sensitive adhesive or the like, relating to a nano thin-film transfer sheet intended to be used as a cosmetic sheet, a moisturizing sheet, a cosmetic aid adhesive sheet, and a cosmetic protective sheet prepared by retaining a cosmetic material or a cosmetic material ingredient.

CITATION LIST

Patent Literature

Patent Literature 1: JP 3215852 B

Non Patent Literature

Non Patent Literature 1: T. Fujie et al., Adv. Funct. Mater., 2009, volume 19, pages 2560-2568

SUMMARY OF INVENTION

Technical Problem

A conventional nano thin-film transfer sheet, when adheres onto an adherend such as the skin, tends to be difficult to handle, for example, fails to adhere homogeneously, because the film shrinks to cause wrinkles, break or falling-off.

Thus, an object of the present invention is to provide a nano thin-film transfer sheet which excels in handleability and is very easy to adhere onto an adherend. It is also an object of the present invention is to provide a method for manufacturing a nano thin-film transfer sheet which excels in handleability and is very easy to adhere onto an adherend as well as a method for transferring the nano thin-film layer of this nano thin-film transfer sheet onto an adherend.

Solution to Problem

The present invention relates to [1] a nano thin-film transfer sheet comprising a permeable base, a soluble support layer, and a nano thin-film layer in this order, wherein the permeable base is a base which allows a solvent dissolving the soluble support layer to permeate or penetrate therethrough.

The present invention also relates to [2] the nano thin-film transfer sheet according to [1], wherein the permeable base is a sheet in mesh-form or porous structure.

The present invention also relates to [3] the nano thin-film transfer sheet according to [1] or [2], wherein the soluble support layer is a layer formed of a polymer dissolvable in water or alcohol.

The present invention also relates to [4] the nano thin-film transfer sheet according to any one of [1] to [3], wherein the nano thin-film layer comprises a layer A formed by using a solution containing a polycation; and a layer B formed by using a solution containing a polyanion.

The present invention also relates to [5] the nano thin-film transfer sheet according to [4], wherein the nano thin-film layer is a layer in which the layer A and the layer B are laminated alternately.

The present invention also relates to [6] the nano thin-film transfer sheet according to [4] or [5], wherein the polycation is a cationic polymer having two or more amino groups in one molecule.

The present invention also relates to [7] the nano thin-film transfer sheet according to any one of [4] to [6], wherein the polyanion is an anionic polymer having two or more carboxyl groups or carboxylate groups in one molecule.

The present invention also relates to [8] the nano thin-film transfer sheet according to any one of [1] to [7], wherein the thickness of the nano thin-film layer is 1 nm to 300 nm.

The present invention also relates to [9] the nano thin-film transfer sheet according to any one of [1] to [8], further comprising a cover film on a surface of the nano thin-film layer opposite to a surface on which the soluble support layer is provided.

Furthermore, the present invention relates to [10] the nano thin-film transfer sheet according to any one of [1] to [9], wherein the nano thin-film layer is for adhesion onto the skin.

The present invention also relates to [11] the nano thin-film transfer sheet according to any one of [1] to [9], wherein the nano thin-film layer is for cosmetic use.

The present invention also relates to [12] a method for manufacturing a nano thin-film transfer sheet comprising a step of allowing a cover film to come into contact with a solution containing a polycation or a solution containing a polyanion to form a layer derived from the polycation or the polyanion on the surface of the cover film; a step of forming a nano thin-film layer by repeating: a step (i) of allowing a polyanion solution to come into contact with the layer derived from the polycation to form a layer derived from the polyanion on the layer derived from the polycation, and a step (ii) of allowing a solution containing the polycation to come into contact with the layer derived from the polyanion to form a layer derived from the polycation on the layer derived from the polyanion; a step of forming a soluble support layer on the nano thin-film layer; and a step of forming a permeable base which allows a solvent dissolving the soluble support layer to permeate or penetrate therethrough on the soluble support layer.

The present invention also relates to [13] the method for manufacturing the nano thin-film transfer sheet according to [12], wherein the steps (i) and (ii) in the step of forming the nano thin-film layer are repeated alternately 1 to 300 times.

The present invention also relates to [14] a method for transferring a nano thin-film layer onto an adherend, comprising a step of allowing the nano thin-film transfer sheet according to any one of [1] to [8] to adhere such that the nano thin-film layer comes in contact with the adherend; and a step of allowing a solvent dissolving the soluble support layer to permeate or penetrate therethrough from the side of the permeable base and then peeling the permeable base off to thereby transfer the nano thin-film layer onto the adherend.

Advantageous Effects of Invention

According to the present invention, it is possible to provide a nano thin-film transfer sheet which excels in handleability and is very easy to adhere onto an adherend. Additionally, according to the present invention, it is possible to provide a method for manufacturing a nano thin-film transfer sheet which excels in handleability and is very easy to adhere onto an adherend as well as a method for transferring the nano thin-film layer of this nano thin-film transfer sheet onto an adherend.

DESCRIPTION OF EMBODIMENTS

Hereinafter, preferable embodiments of the present invention will be described in detail with referring to the drawings as required. However, the present invention is not intended to be limited to the following embodiments. It is noted that dimensional ratios of the drawings are not limited to ratios as shown by the drawings.

The present invention provides a nano thin-film transfer sheet comprising a permeable base, a soluble support layer formed on the permeable base, and a nano thin-film layer formed on the soluble support layer, wherein the permeable base is a base which allows a solvent dissolving the soluble support layer to permeate or penetrate therethrough.

The nano thin-film transfer sheet excels in handleability, toughness (mechanical strength), transparency and moisture retention, and has self-adhesion onto an adherend (for example, the skin) because of the above described constitution. Thus, adhesion onto an adherend is very easy, additionally, the nano thin-film layer after adhesion onto the adherend is inconspicuous, and uncomfortable feeling after adhesion is reduced. It is also possible to use a material of which biodegradability or biocompatibility is high as a material for forming the nano thin-film layer. In this case, there is an advantage that the nano thin-film layer, of which safety is high, is unlikely to cause skin allergy.

Figure 1:
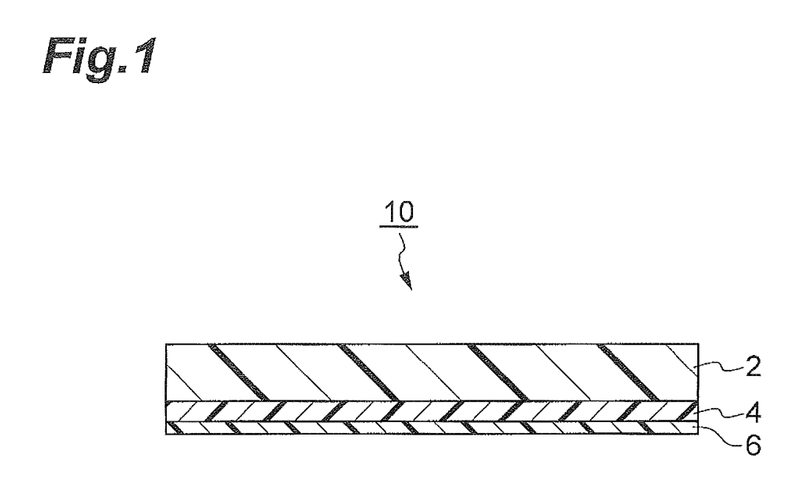
FIG. 1 is a schematic cross-sectional view showing one embodiment of a nano thin-film transfer sheet.

FIG. 1 is a cross-sectional view schematically showing one embodiment of a nano thin-film transfer sheet according to the present invention. The nano thin-film transfer sheet 10 according to the present embodiment comprises a permeable base 2, a soluble support layer 4 and a nano thin-film layer 6 in this order.

[Nano Thin-Film Layer]

It is preferred that the nano thin-film layer 6 according to the present embodiment have a layer A formed by using a solution containing a polycation; and a layer B formed by using a solution containing a polyanion.

The nano thin-film layer 6 is preferably a layer in which the layer A and the layer B are alternately laminated (an alternately laminated thin film). By laminating the layer A and the layer B alternately, a nano thin-film layer which further excels in mechanical strength and self-adhesion is obtained. It is noted that alternately laminating the layer A and the layer B includes not only a case where a single layer A and a single layer B are laminated alternately but also a case where a layer formed of a plurality of layers A and a layer formed of a plurality of layers B are laminated alternately.

(Polycation)

In the present description, the polycation means a compound having two or more cationic groups in one molecule, and the cationic group means a cation group or a group which can be converted to a cation group. Examples of the cationic group include an amino group; a monoalkylamino group such as a methylamino group and an ethylamino group; a dialkylamino group such as a dimethylamino group and a diethylamino group; an imino group and a guanidino group. It is noted that the amino group may be $-NH_3^+$, in which a proton binds via a coordinate bond.

As the polycation, a cationic polymer is preferred. It is noted that, in the present description, the cationic polymer means a polymer having two or more cationic groups in one molecule. As the cationic polymer, one prepared by polymerizing a monomer having a cationic group is preferred.

As the cationic polymer, one which can form a gel-like polyion complex with an anionic polymer described below under the presence of water, can provide the polyion complex having adhesion action to a living tissue, and has less toxic reaction to a living organism is preferred. Moreover, as the cationic polymer, a substance having bioabsorbability is preferred such that the substance is biodegraded and then absorbed in a living organism after a tissue of an affected area is cured.

As the cationic polymer, it is preferred to use a polymer which has such hydrophilicity that the polymer can be dissolved in or swollen with water, and in water, has a property of having a positive electric charge resulting from dissociation of cationic group. As the cationic polymer, a polymer having two or more amino groups in one molecule is especially preferred.

Preferred examples of the cationic polymer include a basic polysaccharide such as collagen, polyhistidine, ionene, chitosan, and aminated cellulose; a homopolymer and a copolymer of a basic amino acid such as polylysine, polyarginine, and a copolymer of lysine and arginine; a basic vinylpolymer such as polyvinylamine, polyallylamine, and polydivinylpyridine; and a salt thereof (a hydrochloride salt, an acetate salt, or the like); polyethyleneimine, polyallylamine hydrochloride, and poly diallyldimethylammonium chloride, or the like.

Also, it is possible to use a cross-linked polymer obtained by cross-linking the above described cationic polymer. As the method of cross-linking the cationic polymer, any of known methods can be used. When the cationic polymer has an amino group, a method of cross-linking by a condensation reaction between the amino group in the cationic polymer and dicarboxylic acid is preferred.

As the cationic polymer, the basic polysaccharide or a derivative thereof (for example, an acetylate or the like), or a salt thereof is preferred. As the basic polysaccharide, chitosan is especially preferred. Chitosan is a deacetylate of chitin, and the deacetylation degree preferably ranges from 40 to 100%, more preferably ranges from 45 to 90%, still more preferably ranges from 50 to 80% because the bioabsorbability and the water solubility become higher.

The molecular weight of the cationic polymer is not particularly limited, but, because the viscosity of the solution containing the polycation becomes higher as the viscosity-average molecular weight is higher, casting tends to be difficult and lamination tends to be difficult at the time of formation of the nano thin-film layer. In the case where the adherend is a living body, the bioabsorbability tends to be decreased when the viscosity-average molecular weight of the cationic polymer is high. The viscosity-average molecular weight of the cationic polymer preferably ranges from 1,000 to 500,000, more preferably ranges from 10,000 to 400,000, still more preferably ranges from 50,000 to 200,000.

In the present description, "viscosity-average molecular weight" may be evaluated by viscometry, which is a general measuring method, and can be calculated, for example, based on an intrinsic-viscosity number [η] measured in accordance with KS K 7367-3: 1999.

As the polycation, even a low molecular compound having two or more cationic groups in one molecule can be preferably used. Examples of the low molecular compound having two or more cationic groups in one molecule include low molecular diamine and polyamine. Specific examples of such polycation include a compound having two amino groups in one molecule such as a diaminoalkane including diaminoethane, diaminopropane, diaminobutane, diaminopentane and diaminohexane; a compound having three to four amino groups in one molecule such as a mono or di lysylaminoalkane including N-(lysyl)-diaminoethane, N,N'-(dilysyl)-diaminoethane, N-(lysyl)-diaminohexane and N,N'-(dilysyl)-diaminohexane; and a compound having five or more amino groups in one molecule.

(Solution Containing Polycation)

In a solution containing the polycation, the concentration of the polycation is preferably 0.01 to 5.0 mass %, more preferably 0.02 to 2.0 mass %, still more preferably 0.05 to 1.0 mass %.

The viscosity of the solution containing the polycation preferably ranges from 0.1 to 1000 mPa·s, more preferably ranges from 0.5 to 500 mPa·s, still more preferably ranges from 1 to 100 mPa·s. In the present description, the viscosity means a value measured by using a tuning fork vibro viscometer SV-10 manufactured by A&D Company, Limited and using 10 mL of a sample at 20° C.

In the solution containing the polycation, two or more types of polycation may be used in combination.

As a solvent used for the solution containing the polycation, any solvent can be used as long as the polycation can be dissolved in the solvent, and water or an aqueous solution of an inorganic salt is appropriate because the charge amount of the polycation can be increased.

It is not necessary to adjust the pH of the solution containing the polycation, and it is possible to directly use a solution prepared by dissolving the polycation in the solvent. For example, it is possible to set the pH of the solution containing the polycation to 1.2 to 6.6.

(Polyanion)

In the present description, the polyanion means a compound having two or more anionic groups in one molecule, and the anionic group means an anion group or a group which can be converted to an anion group. Examples of the anionic, group include a carboxyl group, a carboxylate group, a sulfate group, a sulphonate group, and a phosphate group.

As the polyanion, an anionic polymer is preferred. It is noted that, in the present description, the anionic polymer means a polymer having two or more anionic groups in one molecule. The anionic polymer is preferably one prepared by polymerizing a monomer having an anionic group.

As the anionic polymer, a polymer which can form the gel-like polyion complex with the cationic polymer described above under the presence of water, can provide the polyion complex having adhesion action to a living tissue, and has less toxic reaction to a living organism is preferred. Moreover, as the anionic polymer, a substance having bioabsorbability is preferred such that the substance is biodegraded and then absorbed in a living organism after a tissue of an affected area is cured.

As the anionic polymer, a polymer which has such hydrophilicity that the polymer can be dissolved in or swollen with water, and in water, has a property of having a negative electric charge resulting from dissociation of the anionic group is preferably used. As the anionic polymer, a polymer having two or more carboxyl groups or carboxylate groups in one molecule is especially preferred.

Preferred examples of the anionic polymer include a natural acidic polysaccharide having an anionic group such as a carboxyl group, a carboxylate group or a sulfate group, including alginic acid, hyaluronic acid, chondroitin sulphuric acid, dextran sulphuric acid, pectin and sacran, and a derivative thereof; an acidic polysaccharide artificially synthesized by binding an anionic group to a polysaccharide which naturally does not have an anionic group such as a carboxyl group, a carboxylate group, or a sulfate group, including cellulose, dextran and starch, and a derivative thereof (for example, carboxymethylcellulose, carboxymethyldextran, carboxymethylstarch, carboxymethylchitosan, sulfated cellulose and sulfated dextran, and a derivative thereof); a homopolymer and a copolymer of an acidic amino acid such as polyglutamic acid, polyasparagine acid, and a copolymer of glutamic acid and asparagine acid; an acidic vinyl polymer such as polyacrylic acid; and a salt thereof (for example, an alkali metal salt such as a sodium salt).

Examples of the derivative of the acidic polysaccharide include a compound obtained by reacting the whole or a part of hydroxyl group with acetic acid, nitric acid, sulphuric acid, phosphoric acid or the like; and a compound obtained by esterifying a part of carboxyl group or carboxylate group with a low molecular alcohol such as ethylene glycol and propylene glycol.

Examples of the derivative of the acidic polysaccharide include alginic acid ethylene glycol ester, alginic acid propylene glycol ester, hyaluronic acid ethylene glycol ester, and hyaluronic acid propylene glycol ester. The esterification degree of the derivative is not particularly limited, but when the esterification degree becomes too high, the ratio of the carboxyl group or the carboxylate group, that is, the anionic property decreases, and then, the mechanical strength of the polyion complex which is to be formed with the cationic polymer tends to decrease. Hence, the esterification degree of the derivative of the acidic polysaccharide preferably ranges from 40 to 100%, more preferably ranges from 45 to 90%, still more preferably ranges from 50 to 80%.

Examples of the salt of the acidic polysaccharide or the derivative of the acidic polysaccharide include a salt of the acidic polysaccharide or the derivative of the acidic polysaccharide and a monovalent ion, such as an alkali metal salt including a sodium salt and a potassium salt; and an ammonium salt.

Also, it is possible to use a cross-linked polymer obtained by cross-linking the above described anionic polymer. As the method of cross-linking the anionic polymer, any of known methods can be used. When the anionic polymer has a carboxyl group or a carboxylate group, a method of cross-linking by a condensation reaction of the carboxyl group or the carboxylate group in the anionic polymer with diamine is preferred.

As the anionic polymer, the acidic polysaccharide or the derivative thereof, or the salt thereof is preferred. Especially, alginic acid or the derivative thereof (specifically, alginic acid propylene glycol ester or the like), or the salt thereof (for example, an alkali metal salt such as a sodium salt) is preferred because such compound is a natural polysaccharide, has excellent biocompatibility, and is easily available.

The molecular weight of the anionic polymer is not particularly limited, but, because the viscosity of a solution containing the polyanion becomes higher as the viscosity-average molecular weight is higher, casting tends to be difficult and lamination tends to be difficult at the time of formation of the nano thin-film layer. In the case where the adherend is a living body, the bioabsorbability tends to be decreased when the viscosity-average molecular weight of the anionic polymer is high. The viscosity-average molecular weight of the anionic polymer preferably ranges from 1,000 to 500,000, more preferably ranges from 10,000 to 400,000, still more preferably ranges from 50,000 to 200,000.

As the polyanion, even a low molecular compound having two or more anionic groups in one molecule can be preferably used. Examples of the low molecular compound having two or more anionic groups in one molecule include a compound having two carboxyl groups or carboxylate groups in one molecule such as succinic acid and malonic acid.

(Solution Containing Polyanion)

In a solution containing the polyanion, the concentration of the polyanion is preferably 0.01 to 5.0 mass %, more preferably 0.02 to 2.0 mass %, still more preferably 0.05 to 1.0 mass %.

The viscosity of the solution containing the polyanion preferably ranges from 0.1 to 1000 mPa·s, more preferably ranges from 1 to 500 mPa·s, still more preferably ranges from 3 to 250 mPa·s, especially preferably ranges from 10 to 100 mPa·s.

In the solution containing the polyanion, two or more types of polyanions may be used in combination.

As a solvent used for the solution containing the polyanion, any solvent can be used as long as the polyanion can be dissolved in the solvent, and water or an aqueous solution of an inorganic salt is appropriate because the charge amount of the polyanion can be increased.

The pH of the solution containing the polyanion is preferably 1.6 to 5.4; however, the pH more preferably ranges from 1.8 to 5.0, still more preferably ranges from 2.0 to 4.5, especially preferably ranges from 2.5 to 4.0 because the solubility of the polyanion becomes higher.

The pH of a solution containing the polyanion can be adjusted by adding, for example, an organic acid such as acetic acid, propionic acid, succinic acid, malonic acid, oxalic acid and malic acid, or an inorganic acid such as hydrochloric acid, sulfuric acid and nitric acid.

The combination of the cationic polymer and the anionic polymer may be any combination as long as the cationic polymer and the anionic polymer form the polyion complex and become gelled when mixed under the presence of water. Especially, a combination employing a bioabsorbable polymer as at least one of the cationic polymer and the anionic polymer is preferred because of higher safety.

The bioabsorbable polymer means a polymer which can be biodegraded. Specific examples of such cationic polymer include chitosan, collagen, polylysine, polyarginine, polyhistidine and ionene. Specific examples of such anionic polymer include alginic acid, hyaluronic acid, polyglutamic acid, chondroitin sulphuric acid, and a derivative thereof.

In the case of employing a layer in which the layer A and the layer B are alternately laminated, the number of laminated layers is not particularly limited. The numbers of the layer A and the layer B are both preferably 1 to 300 because the transparency of the nano thin-film layer tends to be maintained easily. Furthermore, the numbers of the layer A and the layer B are both more preferably 10 to 100, still more preferably 20 to 80 because the nano thin-film layer tends to have such a thickness that the thin film has self-adhesion.

A laminate structure composed of the layer A and the layer B in the nano thin-film layer of the present embodiment can be identified by, for example, observing the thin-film layer by IR, NMR, TOF-SIMS, (Time-of-Flight Secondary Ion Mass Spectrometry, Time-of-Flight SIMS), or the like.

The thickness of the nano thin-film layer of the present embodiment is not particularly limited. The thickness of nano thin-film layer preferably ranges from 1 to 300 nm, more preferably ranges from 40 to 300 nm, especially preferably ranges from 40 to 250 nm, most preferably ranges from 40 to 200 nm because properties such as self-adhesion, water absorbability, and flexibility in a dry state become better.

The nano thin-film layer can be suitably used also as a nano thin-film layer for adhesion onto the skin, a nano thin-film layer for cosmetic use, or a nano thin-film layer for cosmetic adhesion onto the skin.

[Soluble Support Layer]

In the present invention, a soluble support layer 4 is not limited as long as the layer can be dissolved in a solvent, but, in consideration of stimulus to the skin, it is preferred that the layer be a layer comprising a film formed of a polymer dissolvable in water or alcohol. The soluble support layer 4 may be a layer dissolvable in a weak acid or weak alkali aqueous solution. That is, the soluble support layer 4 is a dissolvable support film.

Examples of the polymer dissolvable in water or alcohol include polymer electrolytes, such as polyacrylic acid and polymethacrylic acid;

nonionic water-soluble polymers, such as polyethylene glycol, polyacrylamide, polyvinyl alcohol, polyvinyl alcohol derivatives, starch, hydroxypropyl cellulose and cellulose acetate; and resins, such as novolac or poly(N-alkyl-cyanoaciylate).

The molecular weight of the polymer forming the soluble support layer (dissolvable support film) 4 is usually preferably from 100 to 1,000,000, more preferably from 5,000 to 500,000. The molecular weight can be calculated from the average degree of polymerization described below.

In the present embodiment, polyvinyl alcohol or derivatives thereof are more preferably used as a polymer dissolvable in water or alcohol. In the case of employing polyvinyl alcohol, from the viewpoints of film formation and solubility in a solvent, the average degree of polymerization is preferably from 100 to 2,000, more preferably 200 to 1,000. It is herein possible to calculate the average degree of polymerization based on the method specified in HS K 6726.

Also, the thickness of the soluble support layer, from the viewpoints of the releasability from and lamination to the nano thin-film layer, preferably ranges from 1 to 100 μm, more preferably ranges from 2 to 50 μm, still more preferably ranges from 5 to 20 μm.

[Permeable Base]

The permeable base 2 is not limited in its material as long as it is selected from those insoluble in a solvent dissolving the soluble support layer 4. However, the permeable base 2 is a base having a function of allowing the solvent described above to permeate or penetrate therethrough. The permeable base 2 preferably has pores to allow a solvent to permeate or penetrate, and more preferably has a fibrous, mesh-form or porous structure. The permeable base 2 is still more preferably a mesh cloth in which a thread material having a diameter of 100 μm or less is braided into a grid. The permeable base 2 is preferably in the form of a sheet (film) from the viewpoints of handleability and availability.

Examples of the mesh cloth include polyester mesh cloth, nylon mesh cloth, carbon mesh cloth, fluorine resin mesh cloth, polypropylene mesh cloth, silk mesh cloth, and composites of these mesh cloths and non-woven fabric. Of these, polyester mesh cloth, nylon mesh cloth, and polypropylene mesh cloth are preferable, and polyester mesh cloth is more preferable. Examples of the polyester mesh cloth include polyethylene terephthalate mesh cloth.

The opening of the mesh cloth is preferably from 1 to 300 μm, more preferably from 2 to 200 μm, still more preferably from 5 to 150 μm from the viewpoint of transferability.

Also, the opening ratio of the mesh cloth is preferably from 5 to 45%, more preferably from 5 to 40% from the viewpoint of allowing a solvent to permeate or penetrate.

The thickness of the permeable base according to the present embodiment is preferably from 1 to 500 μm, more preferably from 3 to 300 μm, still more preferably from 5 to 200 μm from the viewpoints of conformability and handleability.

[Cover Film]

Figure 2:
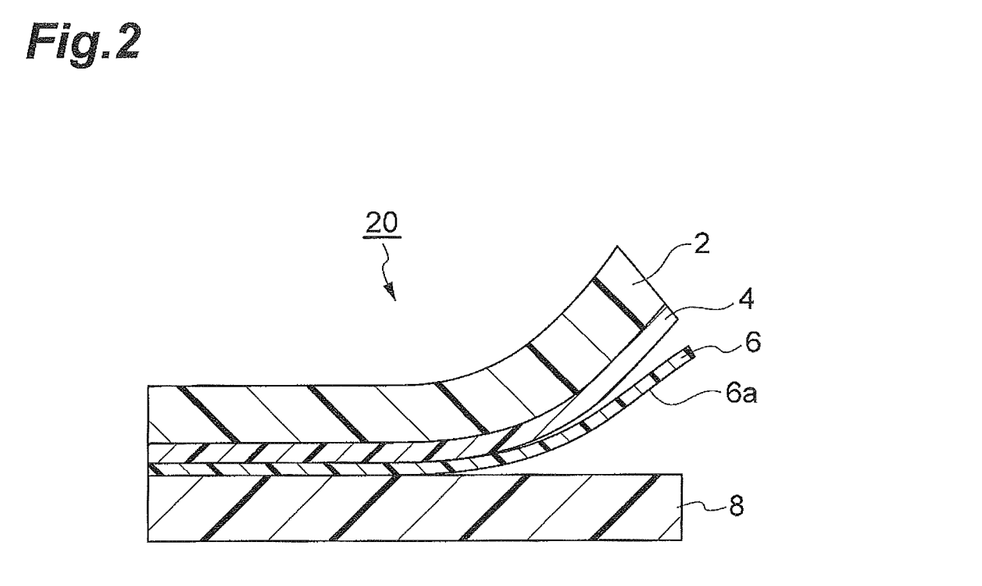
FIG. 2 is a schematic cross-sectional view showing another embodiment of the nano thin-film transfer sheet.

FIG. 2 is a schematic cross-sectional view showing another embodiment of a nano thin-film transfer sheet 20 according to the present invention. The nano thin-film transfer sheet 20 further comprises a cover film 8, in addition to a permeable base 2, a soluble support layer 4, and nano thin-film layer 6. In the present embodiment, in order to protect the nano thin-film layer 6, it is possible to have the cover film 8 on a surface 6a of the nano thin-film layer 6 opposite to the surface on which the soluble support layer 4 is provided (a surface on which a nano thin-film layer is laminated and which is opposite to the nano thin-film layer).

The cover film 8 is not particularly limited as long as it has a smooth surface and may be in the form of a sheet or a roll. As the cover film 8, plastic films, such as polyethylene terephthalate (PET), polyethylene (PE), polypropylene (PP) or polyvinyl chloride (PC) are used suitably.

The cover film 8 can also function as a base for forming the nano thin-film layer 6. It is also possible for the cover film 8 to be a multi-layer nano thin-film transfer sheet by forming the nano thin-film layer 6 on its both sides and providing the soluble support layer 4 and, additionally, the permeable base 2 each on the nano thin-film layer 6. It is convenient because the nano thin-film layers 6 formed on both the surfaces of the cover film 8 can be each used. Hereinafter, the cover film may be referred to as a "base".

The thickness of the cover film 8 preferably ranges from 1 to 500 μm, more preferably ranges from 3 to 300 μm, still more preferably ranges from 5 to 200 μm.

[Method for Manufacturing a Nano Thin-Film Transfer Sheet]

Figure 3:
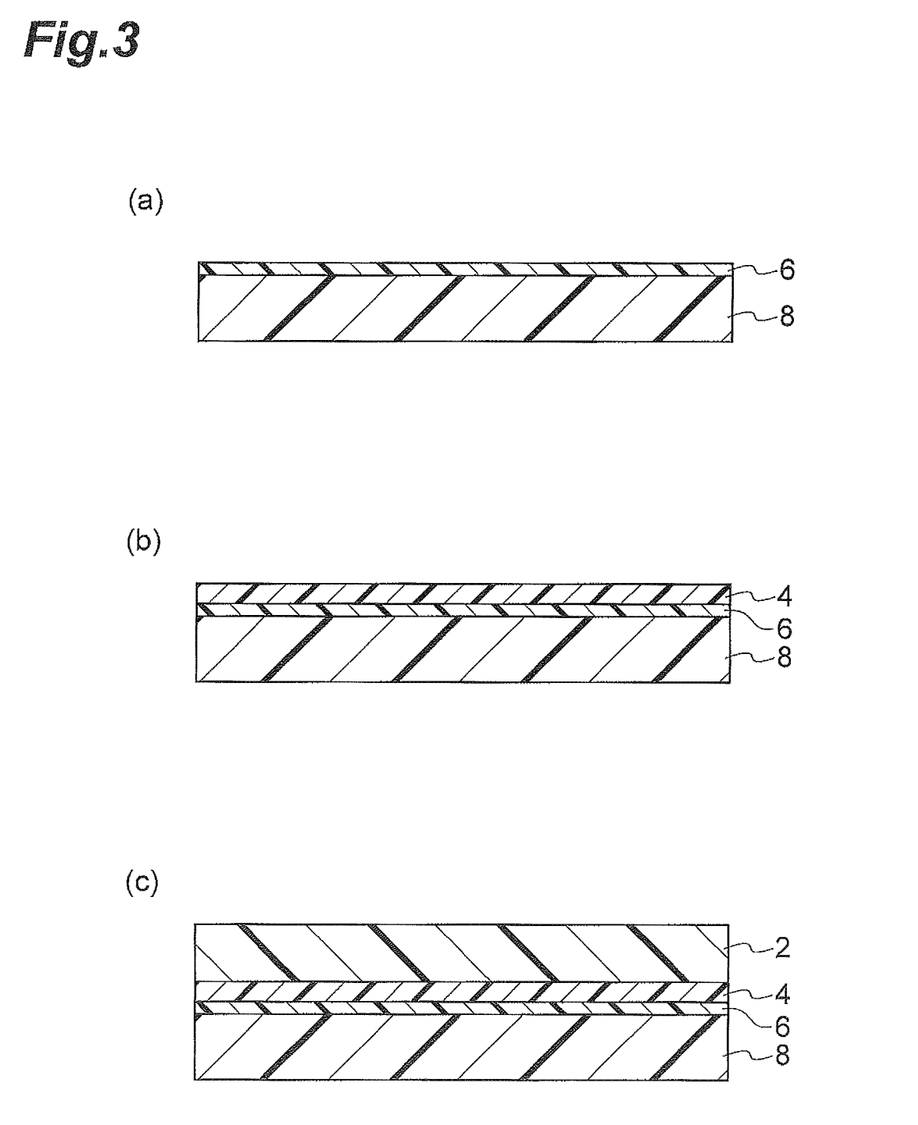
FIG. 3 is a schematic view for describing one embodiment of a method for manufacturing a nano thin-film layer transfer sheet.

The method of manufacturing a nano thin-film transfer sheet of the present embodiment will be described. FIG. 3 is a schematic view for describing one embodiment of the method for manufacturing a nano thin-film layer transfer sheet. The method for manufacturing a nano thin-film transfer sheet comprises a step of allowing a cover film 8 to come into contact with a solution containing a polycation or a solution containing a polyanion to form a layer derived from the polycation or the polyanion on the surface of the cover film; a step of forming a nano thin-film layer 6 by repeating a step (i) of allowing a polyanion solution to come into contact with the layer derived from the polycation to form a layer derived from the polyanion on the layer derived from the polycation and a step (ii) of allowing a solution containing a polycation to come into contact with the layer derived from the polyanion to form a layer derived from the polycation on the layer derived from the polyanion; a step of forming a soluble support layer 4 on the nano thin-film layer 6; and a step of forming a permeable base 2 which allows a solvent dissolving the soluble support layer 4 to permeate or penetrate therethrough on the soluble support layer 4.

(Step of Forming the Nano Thin-Film Layer)

As shown in (a) of FIG. 3, the nano thin-film layer 6 is formed on a base to be the cover film 8. The nano thin-film layer 6 can be manufactured from, for example, a base (cover film), a solution containing a polycation (hereinafter, also referred to as "solution A"), and a solution containing a polyanion (hereinafter, also referred to as "solution B") by alternate lamination disclosed in Langmuir, Vol. 13, pp. 6195-6203 (1997).

Specifically, it is preferred that the method for manufacturing the nano thin-film layer 6 according to the present embodiment comprise a step of allowing a base to be the cover film 8 to come into contact with the solution A or the solution B to form a layer derived from the polycation or the polyanion on the surface of the base (layer formation step); and a step of forming a nano thin-film layer by repeating a step (i) of allowing the solution B to come into contact with the layer derived from the polycation to form a layer derived from the polyanion on the layer derived from the polycation and a step (ii) of allowing the solution A to come into contact with the layer derived from the polyanion to form a layer derived from the polycation on the layer derived from the polyanion.

By this alternate lamination, the layer derived from the polycation (or the layer derived from the polyanion) formed on the base and the solution B (or the solution A) come into contact with each other, and then, the polycation and the polyanion are adsorbed alternately to form a laminated film. Moreover, when the adsorption of the polycation or the polyanion proceeds by the contact and the charge of the surface is inverted, further electrostatic adsorption does not occur, and therefore, the thickness of the layer formed by the contact with the solution A or the solution B can be controlled.

In the nano thin-film layer formation step, the layer derived from the polycation is formed on the surface of the base by allowing the base to come into contact with the solution A, or the layer derived from the polyanion is formed on the surface of the base by allowing the base to come into contact with the solution B. When the surface of the base is negatively charged, it is preferred to conduct the former, and when the surface of the base is positively charged, it is preferred to conduct the latter. At least a part of the surface of the base may be allowed to come into contact with the solution A or the solution B. The contact with the solution A or the solution B may be conducted in two or more installments.

In the step of forming the nano thin-film layer, the charge of the surface may be inverted in the step (i) or the step (ii). The frequency of the contact is not particularly limited. For example, the contact with the solution B may be conducted in two or more installments in the step (i), and the contact with the solution A may be conducted in two or more installments in the step (ii).

The repeating time of the step (i) or the step (ii) in the step of forming the nano thin-film layer is not particularly limited, but it is preferred to repeat those steps until the numbers of the layer derived from the polycation and the layer derived from the polyanion are both 1 to 300 because the transparency of the nano thin-film layer tends to be maintained easily. Moreover, it is more preferred to repeat the steps until the numbers of the layer derived from the polycation and the layer derived from the polyanion are both 10 to 100, especially preferred to repeat the steps until the numbers of the layers are both 20 to 80, because the nano thin-film layer tends to have such a thickness that the nano thin-film layer has self-adhesion. It is noted that the thickness of the nano thin-film layer can be controlled by controlling the repeating time in the step of forming the nano thin-film layer.

In the alternate lamination method, the step of forming the nano thin-film layer preferably ends with the step (ii) rather than with the step (i). By this, the properties of the substance used as the polycation can be exerted more easily. For example, in the case of using chitosan as the polycation, an antibiotic property, which is a property of chitosan, can be exerted more easily.

In the above manufacture method, it is preferred to rinse an adsorbed surface after contact of the base, the layer derived from the polycation or the layer derived from the polyanion with the solution A or the solution B in the layer formation step or the nano thin-film layer formation step. By this, it is possible to remove an extra material from the adsorbed surface.

Preferred examples of a rinse solution used for the rinse include water, an organic solvent, and a mixed solvent of water and a water-soluble organic solvent. Examples of the water-soluble organic solvent include methanol, ethanol, propanol, acetone, dimethylformamide, acetonitrile and the like.

In the manufacturing method, it is preferred to immerse the base, the layer derived from the polycation, or the layer derived from the polyanion into the solution A or the solution B to achieve the contact (hereinafter, also referred to as "alternate immersion method"). For example, in the step of forming the nano thin-film layer, it is preferred to immerse the base into the solution A or the solution B to achieve the contact, and in the laminating step, it is preferred to immerse the layer derived from the polycation (or the layer derived from the polyanion) into the solution B (or the solution A) to achieve the contact. By this, production on an industrial scale is more easily achieved and the manufacturing method can be used more widely.

As a device for forming the laminated film by employing alternate immersion method, a device called a dipper disclosed such as in J. Appl. Phys., Vol. 79, pp. 7501-7509, (1996) and JP 2000-568599 (JP 4302321 B) may be used. In the case of using a dipper, an arm having the base fixed thereon moves automatically, and the base or the like can be immersed in the solution A, the solution B, or the rinse solution sequentially according to a program.

By employing alternate immersion method, it is possible to continue formation of the films as long as the surface charge is inverted. Therefore, the uniformity of the thickness and thickness controllability of the thin film formed by the alternate immersion method is higher than those of a film formed by a conventional dip coating method.

In the case of forming a nano thin-film layer by using the alternate immersion method, it is preferred that the pH of the solution containing the polyanion is from 1.6 to 5.4 from the viewpoint of enabling efficient alternate lamination.

The alternate immersion method can be employed for a base even if the whole or a part of which has a tubular shape, a thread-like shape, a fibrous shape, a foam-like shape, or the like as long as the solution can penetrate into the base by immersion because the laminated film is formed on the surface. Moreover, even if the surface of the base has an uneven shape, the laminated film can be formed by following the surface structure. Furthermore, even if the surface of the base has a nanometer-scale or submicron-scale structure, the laminated film can be formed by following the structure.

The nano thin-film layer 6 of the present embodiment may be manufactured by forming the alternate laminated film by a spin coating method in which the solution A or the solution B is dropped or sprayed on the base. In this case, the rinse solution may be provided by dropping, spraying, shower, or a combination thereof. The base may conduct a movement such as transportation and rotation.

In each case of employing the above described manufacturing methods, as a solvent used for the solution A or the solution B, any solvent can be arbitrarily used as long as the solvent can dissolve the polycation or the polyanion, but water or a aqueous solution of an inorganic salt is appropriate because the charge amount of the polycation or the polyanion can be more increased. The concentration of the polycation or the polyanion in the solution is not particularly limited and may be arbitrarily set depending on the manufacturing method.

Furthermore, in the case where at least one of the polycation and the polyanion is a salt and water solubility of the polycation or the polyanion is decreased by removing a counter ion of the cation group or the anion group in the salt, it is possible to improve the mechanical strength of the nano thin-film layer by removing the counter ion contained in the nano thin-film layer after forming the nano thin-film layer. Removal of the counter ion can be conducted by, for example, increasing the frequency of a cleaning step, immersion into a pH adjusting solution, or the like.

(Step of Forming the Soluble Support Layer).

Subsequently, as shown in (b) of FIG. 3, the soluble support layer 4 is formed on the surface of the nano thin-film layer 6 opposite to the surface on which the cover film 8 is provided.

It is possible to form the soluble support layer 4 by applying a solution of a polymer dissolved in water or alcohol on the nano thin-film layer 6 formed on the cover film 8 and drying the solution usually for 10 minutes to 24 hours, preferably for 1 hour to 12 hours to remove water or alcohol.

Examples of the method for applying the above-described polymer solution on the nano thin-film layer 6 include, but are not limited to, a cast method and a spin coat method. It is also possible to form the nano thin-film layer 6 by using a bar coater or a roll coater.

The concentration of the polymer dissolved in the water or alcohol, is not particularly limited, but, from the viewpoint of coatability, is preferably from 1 to 40 mass %, more preferably from 2 to 30 mass %, still more preferably 5 to 20 mass %, especially preferably from 5 to 10 mass %.

It is possible to peel the soluble support layer (dissolvable support film) 4 off together with the nano thin-film layer 6 from the cover film 8 by using forceps or the like. At this time, it becomes possible to transfer the nano thin-film layer 6 onto the soluble support layer 4, simultaneously with peel-off; by a secondary binding force, such as electrostatic interaction, hydrogen bonding, and van der Waals force, generated between the soluble support layer 4 and the nano thin-film layer 6.

(Step of Forming the Permeable Base)

As shown in (c) of FIG. 3, it is possible to form the permeable base 2 by laminating a material which allows a solvent dissolving the soluble support layer 4 to permeate or penetrate therethrough on the soluble support layer 4. The method for forming the permeable base 2 is not particularly limited, but a method such as lamination or the like can be used. It is noted that the permeable base 2 may be laminated on the soluble support layer 4 after the cover film 8 is removed.

The nano thin-film transfer sheet of the present invention is good in handleability because the permeable base 2 is used. In addition, since the nano thin-film layer 6 is a nanometer-sized thin-film layer, it fits to fine grooves which an adherend has (for example, skin wrinkles or skin fine asperities) or the like to thereby reduce uncomfortable feeling when the nano thin-film layer 6 adheres. Also, when the nano thin-film layer 6 is transparent, the place onto which the layer adheres becomes inconspicuous. In the case where the adherend is the skin, since the layer has self-adhesion to the skin, there is no need to use an adhesive (a pressure-sensitive adhesive) to thereby enable to reduce rashes or rough skin due to the adhesive. In the case of using a biodegradable or biocompatible polymer in the nano thin-film layer 6, the layer has advantages of being unlikely to cause skin allergy when adheres onto the skin and of not adversely affecting on the environment after disposal.

Also, the nano thin-film transfer sheet of the present invention can be suitably used as a cosmetic sheet, a moisturizing sheet, cosmetic aid adhesive sheet, and a cosmetic protective sheet prepared by retaining a cosmetic material or a cosmetic material ingredient.

EXAMPLES

Hereinafter, the present invention will be more specifically described based on Examples and Reference Examples, which by no means limit the present invention.

A chitosan aqueous solution (manufactured by KIMICA corporation: viscosity average molecular weight 90,000, viscosity 12.5 mPa·s, concentration: 0.1 mass %) was used as the cationic polymer, a sodium alginate aqueous solution (manufactured by KIMICA corporation: viscosity average molecular weight 100,000, viscosity 6.7 mPa·s, concentration: 0.1 mass %) was used as the anionic polymer, and malic acid (manufactured by Wako Pure Chemical Industries, Ltd.) was used as the acidic component.

Example 1

As the solution containing a polycation, the 0.1 mass % chitosan aqueous solution was used directly. As the solution containing a polyanion, one obtained by dropping 1 mass part of malic acid (a 1 mass % aqueous solution) relative to 100 mass parts of the 0.1 mass % sodium alginate aqueous solution was used.

A polyethylene terephthalate film (manufactured by TOYOBO CO., LTD., product name "A4100", 150 mm×100 mm×125 μm thickness), which is to be the cover film later, was (a) immersed in the solution containing polycation for 1 minute and then immersed in ultrapure water for rinse (specific resistance 18 MΩ·cm) for 1 minute, and (b) immersed in the solution containing a polyanion for 1 minutes and then immersed in ultrapure water for rinse for 1 minute.

A procedure of repeating (a) and (b) in order was taken as 1 cycle, and this cycle was repeated 30 times, thus forming a nano thin-film layer formed of a layer derived from chitosan and a layer derived from sodium alginate on the polyethylene terephthalate film (the cover film). As the result of measuring the thickness of the formed nano thin-film layer with Model: F20 manufactured by Filmetrics Inc., the thickness was 100 nm.

Subsequently, by using a 10 mass % aqueous solution prepared by dissolving polyvinyl alcohol 500 (manufactured by KANTO CHEMICAL CO., INC., average degree of polymerization=500) in ultrapure water, the solution was applied with a bar coater on the nano thin-film layer such that the thickness after drying achieved 10 μm to thereby form a layer to be the soluble support layer.

Thereafter, as the permeable base, a polyethylene terephthalate mesh sheet (PET mesh, Semitec Corporation, product name "PES45") was overlaid on the layer to be the soluble support layer, and the moisture was evaporated off at room temperature (25° C.). As the result, the nano thin-film transfer sheet in which the nano thin-film layer (alternately laminated film of the layer derived from chitosan and the layer derived from alginic acid), the soluble support layer (polyvinyl alcohol), and the permeable base (polyethylene terephthalate mesh sheet) were sequentially laminated on the cover film (polyethylene terephthalate film) was produced.

Example 2

A nano thin-film transfer sheet was produced by conducting the same process as that in Example 1 except that "PES45" was changed to a polyethylene terephthalate mesh sheet of which opening is different (PET mesh, Semitec Corporation, product name "PET105", opening: 105 μm).

Example 3

A nano thin-film transfer sheet was produced by conducting the same process as that in Example 1 except that "PES45" was changed to a polyethylene terephthalate mesh sheet of which opening is different (PET mesh, Semitec Corporation, product name "PET54", opening: 54 μm).

Example 4

A nano thin-film transfer sheet was produced by conducting the same process as that in Example 1 except that "PES45" was changed to a polyethylene terephthalate mesh sheet of which opening is different (PET mesh, Semitec Corporation, product name "PET15", opening: 15 μm).

Example 5

A nano thin-film transfer sheet was produced by conducting the same process as that in Example 1 except that "PES45" was changed to a polyethylene terephthalate mesh sheet of which opening is different (PET mesh, Semitec Corporation, product name "PET6", opening: 6 μm).

Example 6

A nano thin-film transfer sheet was produced by conducting the same process as that in Example 1 except that "PES45" was changed to a polypropylene mesh sheet of which opening is different (PP mesh, Semitec Corporation, product name "PP140-105", opening: 105 μm).

Example 7

A nano thin-film transfer sheet was produced by conducting the same process as that in Example 1 except that "PES45" was changed to a nylon mesh sheet of which opening is different (nylon mesh, Semitec Corporation, product name "NY60-HD", opening: 60 μm).

Example 8

A nano thin-film transfer sheet was produced by conducting the same process as that in Example 1 except that "polyvinyl alcohol 500", which is the soluble support layer, was changed to "hydroxypropyl cellulose (manufactured by Tokyo Chemical Industry Co., Ltd., 6 to 10 mPa·s (2% in water at 20° C.))".

Example 9

A nano thin-film transfer sheet was produced by conducting the same process as that in Example 1 except that "chitosan", which is the cationic polymer, was changed to "polylysine (manufactured by PEPTIDE INSTITUTE, INC.: molecular weight 120,000, viscosity 3.0 mPa·s, concentration: 0.1 mass %)". In this case, the thickness of the nano thin-film layer was 150 nm.

Example 10

A nano thin-film transfer sheet was produced by conducting the same process as that in Example 1 except that "sodium alginate", which is the anionic polymer, was changed to "sodium hyaluronate (manufactured by Wako Pure Chemical Industries, Ltd.: molecular weight 100,000, viscosity 6.7 mPa·s, concentration: 0.1 mass %)". In this case, the thickness of the nano thin-film layer was 100 nm.

Example 11

A nano thin-film transfer sheet was produced by conducting the same process as that in Example 1 except that "sodium alginate", which is the anionic polymer, was changed to a "sodium chondroitin sulfate aqueous solution (manufactured by Wako Pure Chemical Industries, Ltd.: molecular weight 50,000, viscosity 3.5 mPa·s, concentration: 0.1 mass %). In this case, the thickness of the nano thin-film layer was 240 nm.

Comparative Example 1

A nano thin-film transfer sheet in which the nano thin-film layer (alternately laminated film of the layer derived from chitosan and the layer derived from alginic acid) and the soluble support layer (polyvinyl alcohol) were sequentially laminated on the cover film (polyethylene terephthalate film) was produced in the same manner as Example 1 except that "PES45", which is the permeable base, was not formed.

Comparative Example 2

A nano thin-film transfer sheet in which the nano thin-film layer (alternately laminated film of the layer derived from chitosan and the layer derived from alginic acid) and the permeable base (PES45) were sequentially laminated on the cover film (polyethylene terephthalate film) was produced in the same manner as Example 1 except that the soluble support layer was not formed.

[Transferability Evaluation]

The cover film was peeled off from the nano thin-film transfer sheet of Examples to expose the nano thin-film layer, which was allowed to come into contact with a skin surface so as to face and adhere onto the skin surface. Thereafter, water was dropped onto the permeable base to dissolve the soluble support layer. After 3 minutes, the permeable base was peeled off, and the nano thin-film layer was transferred onto the skin.

The cover film was peeled off from the nano thin-film transfer sheet of Comparative Examples to expose the nano thin-film layer, which was allowed to come into contact with the skin surface so as to face and adhere onto the skin surface. Thereafter, the soluble support layer was dissolved by dropping water thereon. After 3 minutes, when the transferability of the nano thin-film layer onto the skin was checked, a portion of the nano thin-film layer was transferred onto the skin surface, but the major portion of the nano thin-film layer fell off from the skin surface together with the soluble support layer.

Sheets only of which nano thin-film layer was be able to be transferred onto the skin surface without breaking and falling off were "A", and sheets of which nano thin-film layer was broken or fell off were "B". The results are shown in Table 1.

[Evaluation of the Thickness of the Nano Thin-Film Layer after Dissolution of the Soluble Support Layer]

After a nano thin-film transfer sheet of Example 1 to Example 7 and Comparative Example 1 was allowed to adhere onto a 5-inch silicon wafer and the soluble support layer was dissolved, the thickness of the nano thin-film layer transferred on the silicon wafer was measured with Model: F20 manufactured by Filmetrics Inc. The thickness of the transferred nano thin-film layer exhibits better handleability as the difference from the initial thickness of the nano thin-film layer decreases.

TABLE 1

|  | Example | | | | | | | Comparative Example |
|---|---|---|---|---|---|---|---|---|
|  | 1 | 2 | 3 | 4 | 5 | 6 | 7 | 1 |
| Permeable base | PET | PET | PET | PET | PET | PP | Nylon | — |
| Mesh opening (μm) | 45 | 105 | 54 | 15 | 6 | 105 | 60 | — |
| Transferability | A | A | A | A | A | A | A | B |
| Initial thickness of the nano thin-film layer (nm) | 100 | 100 | 100 | 100 | 100 | 100 | 100 | 100 |
| Thickness of the transferred nano thin-film layer (nm) | 101 | 99 | 101 | 118 | 132 | 3000 | 115 | — |

TABLE 2

|  | Example | | | | Comparative Example |
|---|---|---|---|---|---|
|  | 8 | 9 | 10 | 11 | 2 |
| Permeable base | PET | PET | PET | PET | PET |
| Mesh opening (μm) | 45 | 45 | 45 | 45 | 45 |
| Transferability | A | A | A | A | — |
| Initial thickness of the nano thin-film layer (nm) | 100 | 150 | 100 | 240 | 100 |
| Thickness of the transferred nano thin-film layer (nm) | 122 | 158 | 110 | 259 | — |

As shown in Tables 1 and 2, in Examples 1 to 11, in which polyethylene terephthalate mesh sheet, a polypropylene mesh sheet, or a nylon mesh sheet, which is the permeable base, was employed, it is found that the nano thin-film layer can be transferred onto the skin surface without breaking and falling off, excels in transferability, is slightly deformed against water, which is the solvent, and is easy to handle. In contrast, in Comparative Example 1, in which the permeable base is not used, the major portion of the nano thin-film layer fell off from the skin surface. Also, in Comparative Example 2, in which the soluble support layer is not used, transfer was not enabled because the nano thin film failed to be peeled off from the cover film. It is presumed that the thickness of the transferred nano thin-film layer as in Example 6 is larger than the initial thickness of the nano thin-film layer because the soluble support layer is not completely dissolved and remains on the nano thin-film layer.

REFERENCE SIGNS LIST

2: permeable base, 4: soluble support layer, 6: nano thin-film layer, 8: cover film, 10, 20: nano thin-film transfer sheet

The invention claimed is:

1. A nano thin-film transfer sheet comprising a mesh cloth, a soluble support layer, and a nano thin-film layer in this order,
wherein the mesh cloth allows a solvent dissolving the soluble support layer to permeate or penetrate therethrough, and
wherein the mesh cloth includes a cloth selected from the croup consisting of a polyethylene terephthalate mesh cloth, a nylon mesh cloth, a carbon mesh cloth, a fluorine resin mesh cloth, and a polypropylene mesh cloth.

2. The nano thin-film transfer sheet according to claim 1, wherein the soluble support layer is a layer formed of a polymer dissolvable in water or alcohol.

3. The nano thin-film transfer sheet according to claim 1, wherein the nano thin-film layer comprises a layer A formed by using a solution containing a polycation; and a layer B formed by using a solution containing a polyanion.

4. The nano thin-film transfer sheet according to claim 3, wherein the nano thin-film layer is a layer in which the layer A and the layer B are laminated alternately.

5. The nano thin-film transfer sheet according to claim 3, wherein the polycation is a cationic polymer having two or more amino groups in one molecule.

6. The nano thin-film transfer sheet according to claim 3, wherein the polyanion is an anionic polymer having two or more carboxyl groups or carboxylate groups in one molecule.

7. The nano thin-film transfer sheet according to claim 1, wherein a thickness of the nano thin-film layer is from 1 nm to 300 nm.

8. The nano thin-film transfer sheet according to claim 1, further comprising a cover film on a surface of the nano thin-film layer opposite to a surface on which the soluble support layer is provided.

9. The nano thin-film transfer sheet according to claim 1, wherein the nano thin-film transfer sheet is for adhesion onto the skin.

10. The nano thin-film transfer sheet according to claim 1, wherein the nano thin-film transfer sheet is for cosmetic use.

* * * * *